(12) United States Patent
Chang et al.

(10) Patent No.: US 10,274,471 B2
(45) Date of Patent: Apr. 30, 2019

(54) GAS DETECTION MODULE AND GAS SENSOR THEREOF

(71) Applicant: NATIONAL SUN YAT-SEN UNIVERSITY, Kaohsiung (TW)

(72) Inventors: Ting-Chang Chang, Kaohsiung (TW); Hua-Mao Chen, Kaohsiung (TW); Hsiao-Cheng Chiang, Kaohsiung (TW); Yu-Ching Tsao, Kaohsiung (TW); Min-Chen Chen, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 250 days.

(21) Appl. No.: 15/471,760

(22) Filed: Mar. 28, 2017

(65) Prior Publication Data
US 2018/0136154 A1 May 17, 2018

(30) Foreign Application Priority Data
Nov. 15, 2016 (TW) .............................. 105137327 A

(51) Int. Cl.
*H01L 29/786* (2006.01)
*G01N 33/497* (2006.01)
(Continued)

(52) U.S. Cl.
CPC ..... *G01N 33/0047* (2013.01); *G01N 27/4141* (2013.01); *G01N 33/4972* (2013.01); *H01L 29/24* (2013.01); *H01L 29/7869* (2013.01)

(58) Field of Classification Search
USPC ................. 422/83–88; 73/23.3, 23.4, 335.05
See application file for complete search history.

(56) References Cited

U.S. PATENT DOCUMENTS 4,354,308 A * 10/1982 Shimada .............. G01N 27/414
                                                                    204/400
5,324,683 A *  6/1994 Fitch ................... G01P 15/0802
                                                                    148/DIG. 73
(Continued)

FOREIGN PATENT DOCUMENTS

CN       102290445 A    12/2011
TW       I256169         6/2003
TW       I373137 B       9/2012

OTHER PUBLICATIONS

English abstract translation of TW patent I256169 dated Jun. 24, 2003.

*Primary Examiner* — Brian R Gordon
(74) *Attorney, Agent, or Firm* — WPAT, PC

(57) ABSTRACT

A gas detection module is provided with a convenient detection mechanism of the alcohol gas. The gas detection module may include a gas sensor and a detection circuit. The gas sensor includes a substrate, a gate, an insulating layer, an active layer, a source and a drain. The gate is disposed on the substrate. The insulating layer is disposed on the gate and the substrate. The active layer is disposed on the insulating layer. Each of the source and the drain is partially arranged on the active layer and extends to the insulating layer. The active layer is exposed from between the source and the drain. The detection circuit is electrically connected to the source of the gas sensor. Based on this, the deficiency of the conventional gas detection module can be overcome.

16 Claims, 4 Drawing Sheets

(51) Int. Cl.
*G01N 33/00* (2006.01)
*H01L 29/24* (2006.01)
*G01N 27/414* (2006.01)

(56) References Cited

U.S. PATENT DOCUMENTS

| | | | | |
|---|---|---|---|---|
| 5,944,970 A * | 8/1999 | Rosenblatt | ......... | G01N 27/4148 204/416 |
| 6,111,280 A * | 8/2000 | Gardner | ......... | G01N 27/128 257/253 |
| 7,145,174 B2 * | 12/2006 | Chiang | ......... | H01L 29/7869 257/59 |
| 7,242,039 B2 * | 7/2007 | Hoffman | ......... | H01L 29/7869 257/213 |
| 7,250,627 B2 * | 7/2007 | Hoffman | ......... | H01L 29/7869 257/59 |
| 7,297,977 B2 * | 11/2007 | Hoffman | ......... | H01L 29/7869 257/43 |
| 7,642,573 B2 * | 1/2010 | Hoffman | ......... | H01L 29/7869 257/192 |
| 7,868,354 B2 * | 1/2011 | Garcia | ......... | G01N 33/0037 257/192 |
| 8,013,363 B2 * | 9/2011 | Bertin | ......... | B82Y 10/00 257/206 |
| 8,152,991 B2 * | 4/2012 | Briman | ......... | G01N 27/127 205/775 |
| 8,217,490 B2 * | 7/2012 | Bertin | ......... | B82Y 10/00 257/209 |
| 8,415,166 B2 * | 4/2013 | Naaman | ......... | G01N 27/126 257/253 |
| 8,809,861 B2 * | 8/2014 | Le Neel | ......... | H01L 29/66742 257/213 |
| 9,103,775 B2 * | 8/2015 | Bradley | ......... | B82Y 10/00 |
| 9,196,615 B2 * | 11/2015 | Bertin | ......... | B82Y 10/00 |
| 9,287,356 B2 * | 3/2016 | Bertin | ......... | H01L 29/861 |
| 9,911,743 B2 * | 3/2018 | Bertin | ......... | B82Y 10/00 |
| 2007/0087564 A1 * | 4/2007 | Speakman | ......... | H01G 9/2031 438/674 |
| 2007/0092770 A1 | 4/2007 | Obata et al. | | |
| 2008/0063566 A1 * | 3/2008 | Matsumoto | ......... | G01N 33/5438 422/68.1 |
| 2011/0168994 A1 * | 7/2011 | Kawashima | ......... | C04B 35/01 257/43 |
| 2011/0169057 A1 * | 7/2011 | Tsukada | ......... | G01N 27/4141 257/253 |
| 2012/0217550 A1 * | 8/2012 | Usagawa | ......... | G01N 27/4141 257/253 |
| 2012/0223370 A1 | 9/2012 | Zan et al. | | |
| 2013/0009149 A1 * | 1/2013 | Endo | ......... | H01L 27/1218 257/43 |
| 2013/0181854 A1 * | 7/2013 | Koyama | ......... | G11C 27/026 341/122 |
| 2013/0217598 A1 * | 8/2013 | Ludwig | ......... | G01N 33/54373 506/16 |
| 2014/0121787 A1 * | 5/2014 | Yamazaki | ......... | H04L 12/2825 700/19 |
| 2016/0094236 A1 * | 3/2016 | Shionoiri | ......... | H03M 1/002 341/122 |
| 2016/0293342 A1 * | 10/2016 | Yumoto | ......... | H01G 9/2031 |
| 2017/0168000 A1 | 6/2017 | Ichiki | | |
| 2017/0213821 A1 * | 7/2017 | Or-Bach | ......... | H01L 21/48 |
| 2018/0136157 A1 * | 5/2018 | Harada | ......... | G01N 27/127 |
| 2019/0011415 A1 * | 1/2019 | Nemirovsky | ...... | G01N 33/0027 |

\* cited by examiner

GAS DETECTION MODULE AND GAS SENSOR THEREOF

CROSS REFERENCE TO RELATED APPLICATIONS

The application claims the benefit of Taiwan application serial No. 105137327, filed on Nov. 15, 2016, and the subject matter of which is incorporated herein by reference.

BACKGROUND OF THE INVENTION

1. Field of the Invention

The present disclosure generally relates to a gas detection module and, more particularly, to a gas detection module that detects alcohol gas.

2. Description of the Related Art

Gas sensors are widely used in daily life and can be used to detect the noxious gas (such as carbon monoxide) or the hazardous gas (such as alcohol gas). As an example of the alcohol gas, the gas sensor can help the police to detect the alcohol concentration of the drivers by ways of blow test or blood test. As a result, the police can clamp down on the drunk driving behaviors and reduce the accident casualty resulting from drunk driving behaviors.

The conventional alcohol concentration sensor may be formed using an ethanol fuel cell, and includes a polymer film and a concentration detecting portion. The polymer film is proton conductive. When the polymer film is dipped in the alcohol-containing liquid, the proton conductivity of the polymer film can change based on the alcohol concentration of the liquid. As such, the concentration detecting portion can detect the alcohol concentration of the liquid according to the change of the proton conductivity of the polymer film. One embodiment of such an alcohol concentration sensor can be seen in Taiwan Patent No. 1256169 entitled "Method of measuring the concentration of alcohol, device for measuring concentration of alcohol and fuel cell system containing the device."

However, the conventional alcohol concentration sensor can only detect the alcohol concentration of the liquid. Although the alcohol in the liquid always dissipates into the air so that some equations can be used to calculate the alcohol concentration of the liquid, this approach requires the alcohol to be placed in a closed chamber and it takes a certain period of time for the alcohol to dissipate into the air. As such, the detection of the alcohol concentration is slow and inefficient, therefore this approach is not suitable for blow test. In addition, the alcohol concentration varies with the proton conductivity of the liquid. Thus, the detection accuracy of the alcohol concentration may be affected after the polymer film, which has the proton conductivity, has been used for a long period of time.

In light of the deficiency, it is necessary to improve the conventional alcohol concentration sensor.

SUMMARY OF THE INVENTION

It is therefore the objective of this disclosure to provide a gas detection module capable of quickly detecting a predetermined gas.

In an embodiment, a gas sensor is disclosed. The gas sensor may include a substrate, a gate, an insulating layer, an active layer, a source and a drain. The gate is disposed on the substrate. The insulating layer is disposed on the gate and the substrate. The active layer is disposed on the insulating layer. Each of the source and the drain is partially arranged on the active layer and extends to the insulating layer. The active layer is exposed from between the source and the drain.

In another embodiment, a gas detection module is disclosed. The gas detection module may include a gas sensor and a detection circuit. The gas sensor includes a substrate, a gate, an insulating layer, an active layer, a source and a drain. The gate is disposed on the substrate. The insulating layer is disposed on the gate and the substrate. The active layer is disposed on the insulating layer. Each of the source and the drain is partially arranged on the active layer and extends to the insulating layer. The active layer is exposed from between the source and the drain. The detection circuit includes an operational amplifier, a resistor and an electrical sensor. The operational amplifier includes two input ends and an output end. A first one of the two input ends is electrically connected to a ground end, and a second one of the two input ends is electrically connected to the source of the gas sensor. The second one of the two input ends is electrically connected to the output end via the resistor. The electrical sensor is electrically connected between the output end and the ground end.

The gas sensor may be a back-channel-etch thin-film transistor. The active layer may be made of a material which is an oxide of at least one of elements including hafnium, stannum, zinc, gallium, tungsten, indium, silicon and aluminum. The concentration ratio between oxygen ions and non-oxygen ions of the active layer may be 1:1. The active layer may be formed by indium gallium zinc oxide. The content ratio of indium, gallium, zinc and oxygen may be 1:1:1:4. The active layer has an energy gap of 1.5-4.5 eV. As such, the gas detection module of the disclosure can detect the predetermined gas via the sensing area, and the sensing signal is outputted upon the detection of the predetermined gas.

The source may output an induced electric current which is converted into an induced voltage by the resistor, and the electrical sensor detects the induced voltage. The electrical sensor outputs an indication signal when the induced electric current is larger than a threshold current value by a predetermined amount. As such, the detection circuit can detect the magnitude of the sensing signal in order to determine the concentration of the predetermined gas. Based on different magnitudes of the sensing signals generated by different gases, incorrect determination can be avoided.

With the gas detection module and its gas sensor, the gas sensor can detect the predetermined gas via the sensing area of the gas sensor. The sensing signal is outputted upon the detection of the predetermined gas. The detection circuit can detect the magnitude of the sensing signal in order to determine the concentration of the predetermined gas. Based on different magnitudes of the sensing signals generated by different gases, incorrect determination can be avoided. Therefore, the gas detection module of the disclosure can provide a convenient gas detection and avoid incorrect determination, thereby meeting the requirement of daily use and improving the life quality of the users.

BRIEF DESCRIPTION OF THE DRAWINGS

The present disclosure will become more fully understood from the detailed description given hereinafter and the accompanying drawings which are given by way of illustration only, and thus are not limitative of the present disclosure, and wherein.

Figure 1:
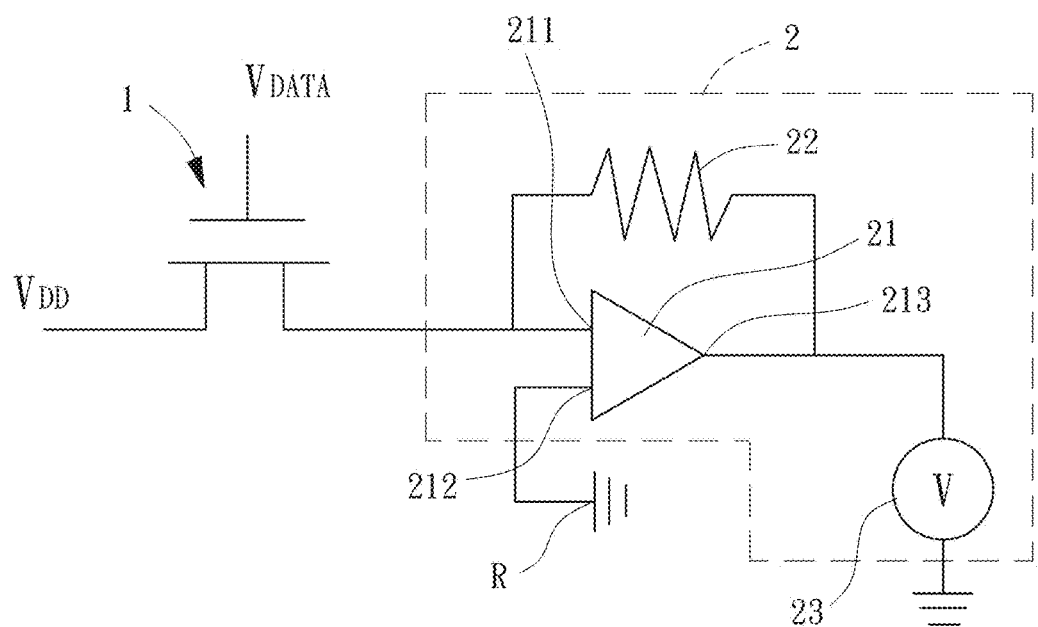
FIG. 1 shows a circuit diagram of a gas detection module according to an embodiment of the disclosure.

In the various figures of the drawings, the same numerals designate the same or similar parts. Furthermore, when the terms "first", "second", "third", "fourth", "inner", "outer", "top", "bottom", "front", "rear" and similar terms are used hereinafter, it should be understood that these terms have reference only to the structure shown in the drawings as it would appear to a person viewing the drawings, and are utilized only to facilitate describing the disclosure.

DETAILED DESCRIPTION OF THE INVENTION

Figure 2:
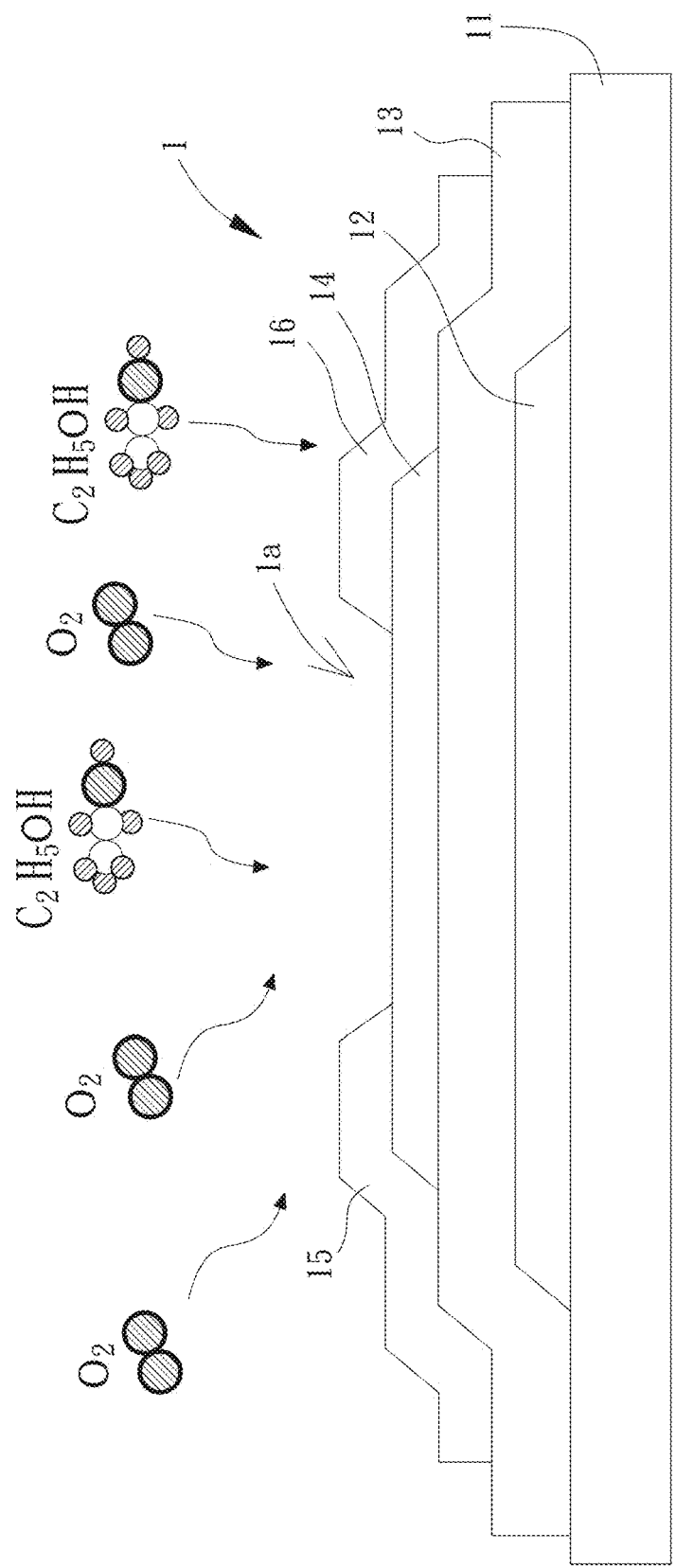
FIG. 2 is a cross sectional view of the gas detection module according to the embodiment of the disclosure.

FIGS. 1 and 2 show a gas detection module according to an embodiment of the disclosure. The gas detection module includes a gas sensor 1 and a detection circuit 2 electrically connected to the gas sensor 1. The gas sensor 1 has a sensing area 1a on a surface thereof. The detection circuit 2 can output a sensing signal when the gas sensor 1 senses a predetermined gas. In this embodiment, the gas sensor 1 may be a thin-film transistor such as a back-channel-etch (BCE) thin-film transistor.

As an example of a BCE thin-film transistor shown in FIG. 2, the gas sensor 1 may include a substrate 11, a gate 12, an insulating layer 13, an active layer 14, a source 15 and a drain 16. The substrate 11 may be the one used in a conventional thin-film transistor, such as a glass substrate. The substrate 11 is used for placement of other material layers. The gate 12 may be disposed on the substrate 11. The gate 12 may be formed by the deposition of titanium/aluminum/titanium. The insulating layer 13 may be disposed on the gate 12. The insulating layer 13 may be formed by the deposition of an insulating material such as silicon dioxide or silicon nitride. The active layer 14 can cover the insulating layer 13 and can be made by deposing a material or composition having an energy gap of 1.5-4.5 eV. The active layer 14 is made of a material which is the oxide of at least one of the elements including hafnium (Hf), stannum (Sn), zinc (Zn), gallium (Ga), tungsten (W), indium (In), silicon (Si) and aluminum (Al). The concentration ratio between oxygen ions and non-oxygen ions may be 1:1. In this example, the active layer 14 may be formed by indium gallium zinc oxide (InGaZno), in which the content ratio of indium, gallium, zinc and oxygen may be 1:1:1:4. The source 15 and the drain 16 can be partially arranged on the active layer 14 and extend to the insulating layer 13. Titanium/aluminum/titanium can be deposited on the active layer 14 and etched to form the source 15 and the drain 16, permitting the active layer 14 to be exposed from between the source 15 and the drain 16 and to form the sensing area 1a. However, this is not used to limit the disclosure.

Referring to FIG. 1 again, the detection circuit 2 may include an operational amplifier 21, a resistor 22 and an electrical sensor 23. The operational amplifier 21 includes two input ends 211 and 212 (such as positive and negative input ends) and an output end 213. One of the two input ends 211 and 212 (such as the negative input end) may be electrically connected to a ground end R. Another of the two input ends 211 and 212 (such as the positive input end) may be electrically connected to the source 15 of the gas sensor 1, and to the output end 213 via the resistor 22. The electrical sensor 23 may be electrically connected between the output end 213 and the ground end R. In this example, the electrical sensor 23 (such as a voltage sensor) may be used to detect an induced electric current outputted by the source 15. The electric current may be converted into an induced voltage by the resistor 22, and the voltage can be detected by the electrical sensor 23. If the induced electric current is larger than a threshold current value by a certain amount (such as ten to tens times larger), the electrical sensor 23 may output an indication signal. The indication signal may be in the form of light, color, context, pattern or sound according to the requirement. However, this is not used to limit the disclosure.

Referring to FIG. 1 again, during the use of the gas detection module according to the embodiment of the disclosure, the drain 16 of the gas sensor 1 may be connected to an external DC power $V_{DD}$ in order to acquire the power needed for the operations of the gas sensor 1. This permits the gas sensor 1 to operate in the saturation region of the operation curve. Since the operational amplifier 21 has an extremely large input resistance, the two input ends 211 and 212 of the operational amplifier 21 may be regarded as having equal potential. If the two input ends 211 and 212 are respectively connected to the ground end R and the source 15, the source 15 can be regarded as being grounded.

Based on this, referring to FIG. 1, the sensing area 1a on the active layer 14 can serve as a data input end used to receive a voltage $V_{DATA}$. When the sensing area 1a is exposed to different kinds of gases, the active layer 14 may have different chemical reactions and accordingly generate different induced voltages $V_{DATA}$. Thus, different amounts of electric charges can be generated between the source 15 and the drain 16, permitting the drain 16 to output different induced electric currents. The electric currents can then be used to determine the concentration of the gas and can be converted into different induced voltages for different applications. In this example, the active layer 14 is repeatedly fed with alcohol gas ($C_2H_5OH$) and oxygen ($O_2$) to observe the changes of the induced electric currents. However, this example is not used to limit the disclosure.

Figure 3:
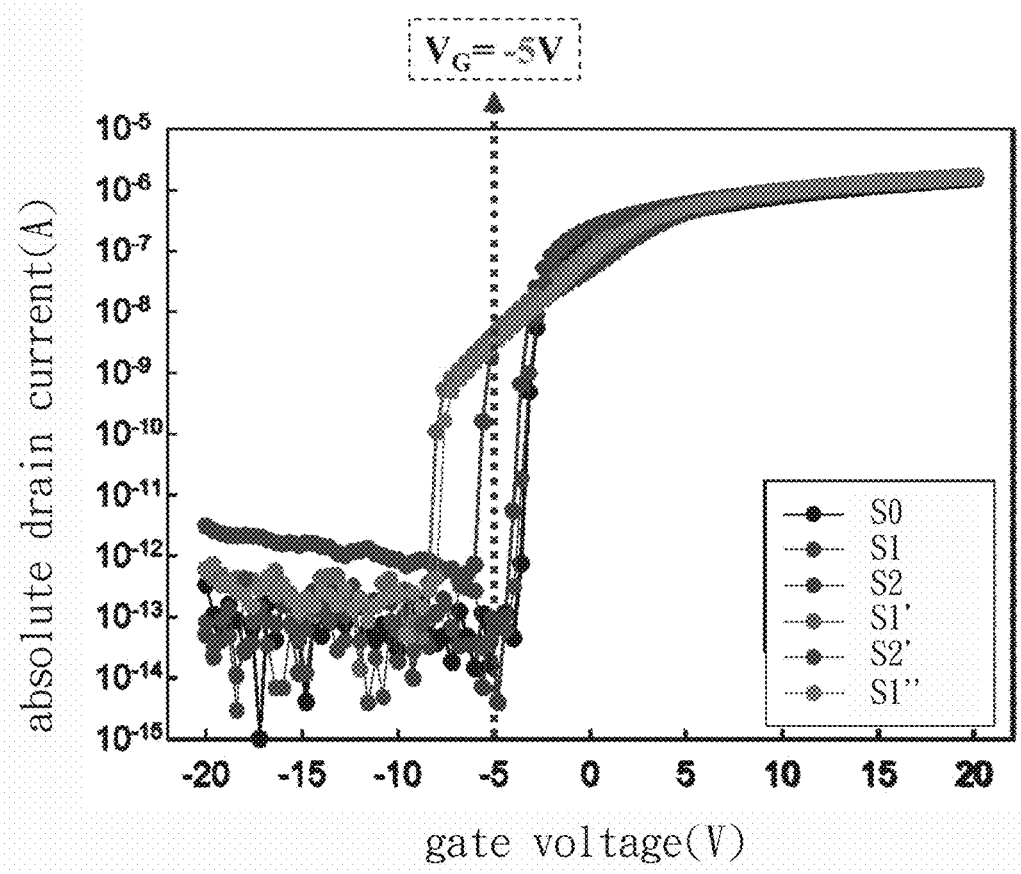
FIG. 3 shows the current-voltage characteristic curves of the gas detection module when used to detect oxygen and alcohol gas.
Figure 4:
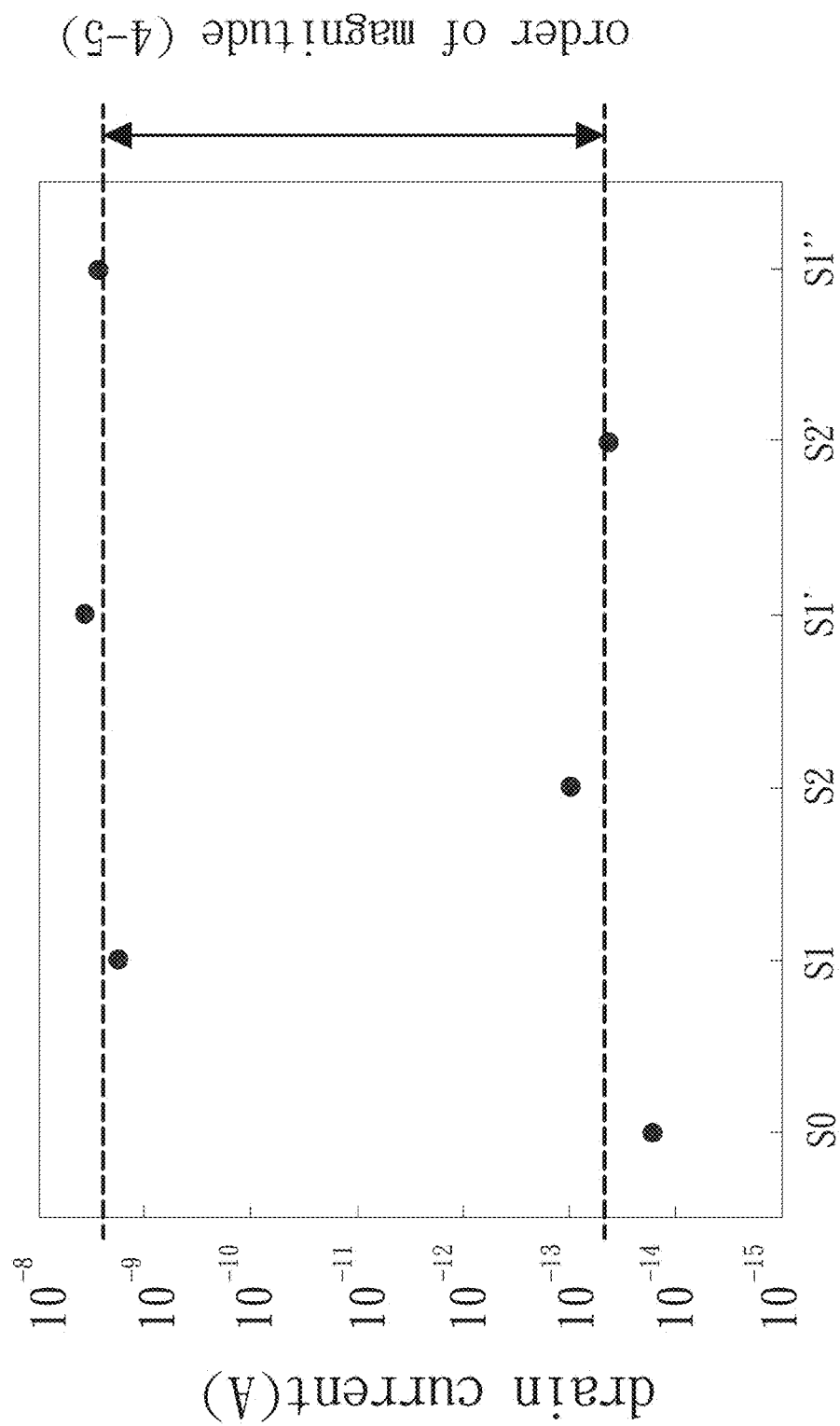
FIG. 4 shows the induced electric currents when the gas detection module is used to detect the oxygen and alcohol gas.

FIG. 3 shows the current-voltage characteristic curves of the gas detection module when used to detect oxygen and alcohol gas. FIG. 4 shows the induced electric currents when the gas detection module is used to detect the oxygen and alcohol gas. The characteristic curves represent the electric currents respectively in the initial state (S0), the first alcohol state in which the alcohol is applied for the first time (S1), the first oxygen state in which the oxygen is applied for the first time (S2), the second alcohol state in which the alcohol is applied for the second time (S1'), the second oxygen state in which the oxygen is applied for the second time (S2'), and the third alcohol state in which the alcohol is applied for the third time (S1").

Referring to FIG. 3, when the alcohol gas is applied for the first time, the initial voltage $V_G$ of the active layer 14 will shift to the left on the voltage axis (as is shown in FIG. 3 $V_G$=−5V). The voltage $V_G$ will restore its original value when the oxygen is applied for the first time. However, when the alcohol gas is applied for the second time, the voltage $V_G$ of the active layer 14 still shifts to the left on the voltage axis. When the oxygen is applied for the second time, the voltage $V_G$ still restores its original value. Similarly, when the alcohol gas is applied for the third time, the voltage $V_G$ of the active layer 14 shifts to the left on the voltage axis again. Based on the fact that voltage $V_G$ changes with the applied gases, the magnitude of the change can be converted into the concentration of the alcohol gas.

Referring to FIG. 4, when the gate 12 of the active layer 14 is fed with a voltage of −5V (such as $V_G$=−5V in FIG. 3) in which the alcohol gas and oxygen are repeatedly fed into the gas detection module in turn, it can be observed that the difference in the magnitudes of the electric currents can be as high as $1*10^{4-5}$ times (the difference between presence and absence of the alcohol gas). Thus, the measured result of the alcohol gas is highly distinguishing from the results of other kinds of gases. Therefore, the gas detection module of the disclosure can effectively detect the predetermined gas and avoid incorrect detection. Based on this, the gas detection module has a high sensitivity of gas detection. In addition, the production machine of the gas detection module is compatible with the currently-used production machine, such that it can be directly used in the optoelectronics industry. As such, the displays can have a higher added value.

Based on this, the gas detection module according to the embodiment of the disclosure can detect the predetermined gas via the sensing area. The sensing signal is outputted upon the detection of the predetermined gas. The detection circuit can detect the magnitude of the sensing signal in order to determine the concentration of the predetermined gas. Based on different magnitudes of the sensing signals generated by different gases, incorrect determination can be avoided. Therefore, the gas detection module of the embodiment of the disclosure can provide a convenient gas detection and avoid incorrect determination, thereby meeting the requirement of daily use and improving the life quality of the users.

Although the disclosure has been described in detail with reference to its presently preferable embodiments, it will be understood by one of ordinary skill in the art that various modifications can be made without departing from the spirit and the scope of the disclosure, as set forth in the appended claims.

What is claimed is:

1. A gas detection module comprising:
    a gas sensor having a substrate, a gate, an insulating layer, an active layer, a source and a drain, wherein the gate is disposed on the substrate, wherein the insulating layer is disposed on the gate and the substrate, wherein the active layer is disposed on the insulating layer, wherein each of the source and the drain is partially arranged on the active layer and extends to the insulating layer, and wherein the active layer is exposed from between the source and the drain; and
    a detection circuit comprising an operational amplifier, a resistor and an electrical sensor, wherein the operational amplifier comprises two input ends and an output end, wherein a first one of the two input ends is electrically connected to a ground end, wherein a second one of the two input ends is electrically connected to the source of the gas sensor, wherein the second one of the two input ends is electrically connected to the output end via the resistor, and wherein the electrical sensor is electrically connected between the output end and the ground end.

2. The gas detection module as claimed in claim 1, wherein the active layer is made of a material which is an oxide of at least one of elements including hafnium, stannum, zinc, gallium, tungsten, indium, silicon and aluminum.

3. The gas detection module as claimed in claim 2, wherein a concentration ratio between oxygen ions and non-oxygen ions of the active layer is 1:1.

4. The gas detection module as claimed in claim 2, wherein the active layer is formed by indium gallium zinc oxide.

5. The gas detection module as claimed in claim 4, wherein a content ratio of indium, gallium, zinc and oxygen is 1:1:1:4.

6. The gas detection module as claimed in claim 1, wherein the active layer has an energy gap of 1.5-4.5 eV.

7. The gas detection module as claimed in claim 1, wherein the gas sensor is a back-channel-etch thin-film transistor.

8. The gas detection module as claimed in claim 1, wherein the source outputs an induced electric current which is converted into an induced voltage by the resistor, wherein the electrical sensor detects the induced voltage.

9. The gas detection module as claimed in claim 8, wherein the electrical sensor outputs an indication signal when the induced electric current is larger than a threshold current value by a predetermined amount.

10. A gas sensor comprising:
    a substrate, a gate, an insulating layer, an active layer, a source and a drain, wherein the gate is disposed on the substrate, wherein the insulating layer is disposed on the gate and the substrate, wherein the active layer is disposed on the insulating layer, wherein each of the source and the drain is partially arranged on the active layer and extends to the insulating layer, and wherein the active layer is exposed from between the source and the drain.

11. The gas sensor as claimed in claim 10, wherein the active layer is made of a material which is an oxide of at least one of elements including hafnium, stannum, zinc, gallium, tungsten, indium, silicon and aluminum.

12. The gas sensor as claimed in claim 11, wherein a concentration ratio between oxygen ions and non-oxygen ions of the active layer is 1:1.

13. The gas sensor as claimed in claim 11, wherein the active layer is formed by indium gallium zinc oxide.

14. The gas sensor as claimed in claim 13, wherein a content ratio of indium, gallium, zinc and oxygen is 1:1:1:4.

15. The gas sensor as claimed in claim 10, wherein the active layer has an energy gap of 1.5-4.5 eV.

16. The gas sensor as claimed in claim 10, wherein the gas sensor is a back-channel-etch thin-film transistor.

* * * * *